United States Patent
Rafaeli et al.

(10) Patent No.: US 10,159,456 B2
(45) Date of Patent: Dec. 25, 2018

(54) SYSTEMS AND METHODS FOR BIOPSY GUIDANCE USING A BIOPSY UNIT INCLUDING AT LEAST ONE OF AN IMAGING DETECTOR OR ULTRASOUND PROBE CONCURRENTLY MOUNTED WITH A BIOPSY GUIDE

(71) Applicant: General Electric Company, Schenectady, NY (US)

(72) Inventors: Tzachi Rafaeli, Shlmenit (IL); Ira Micah Blevis, Zicron Yaakov (IL)

(73) Assignee: GE MEDICAL SYSTEMS ISRAEL, LTD, Brookfield, WI (US)

( * ) Notice: Subject to any disclaimer, the term of this patent is extended or adjusted under 35 U.S.C. 154(b) by 881 days.

(21) Appl. No.: 13/683,926

(22) Filed: Nov. 21, 2012

(65) Prior Publication Data
US 2013/0223590 A1   Aug. 29, 2013

Related U.S. Application Data

(60) Provisional application No. 61/562,839, filed on Nov. 22, 2011.

(51) Int. Cl.
*A61B 5/00* (2006.01)
*A61B 6/00* (2006.01)
*A61B 8/08* (2006.01)

(52) U.S. Cl.
CPC ............ *A61B 6/502* (2013.01); *A61B 6/4258* (2013.01); *A61B 6/4417* (2013.01); *A61B 8/0841* (2013.01)

(58) Field of Classification Search
CPC ............ G01T 1/161; G01T 1/164; G01T 1/00
USPC .......................................................... 382/128
See application file for complete search history.

(56) References Cited

U.S. PATENT DOCUMENTS

| | | | |
|---|---|---|---|
| 5,252,830 A | 10/1993 | Weinberg | |
| 5,961,457 A | 10/1999 | Raylman et al. | |
| 6,490,467 B1 | 12/2002 | Bucholz et al. | |
| 7,102,134 B2 | 9/2006 | Weinberg | |
| 7,711,409 B2 | 5/2010 | Keppel et al. | |
| 8,050,743 B2* | 11/2011 | Daghighian ................... | 600/431 |
| 2006/0106306 A1* | 5/2006 | Essner et al. ................. | 600/436 |
| 2006/0224149 A1 | 10/2006 | Hillely | |

(Continued)

OTHER PUBLICATIONS

Amanda L. Weinmann, et al., Design of Optimal Collimation for Dedicated Molecular Breast Imaging Systems, Med. Phys. 36 (3), Feb. 19, 2009, pp. 845-856.

(Continued)

*Primary Examiner* — Rajeev Siripurapu
(74) *Attorney, Agent, or Firm* — Dean D. Small; The Small Patent Law Group, LLC

(57) ABSTRACT

Systems and methods for biopsy guidance are provided. One system includes a gantry and a breast immobilization plate mounted to the gantry, wherein the breast immobilization plate is configured to be coupled with a biopsy unit. The biopsy unit includes at least one nuclear medicine imaging detector in an angled orientation with respect to the breast immobilization plate. The breast imaging system also includes a nuclear medicine imaging detector mounted to the gantry parallel to the breast immobilization plate, wherein the nuclear medicine imaging detector mounted to the gantry and the breast immobilizing plate are configured to immobilize a breast therebetween.

6 Claims, 6 Drawing Sheets

(56) References Cited

U.S. PATENT DOCUMENTS

| | | |
|---|---|---|
| 2008/0084961 A1 | 4/2008 | Keppel et al. |
| 2008/0086059 A1 | 4/2008 | Keppel et al. |
| 2009/0163830 A1 | 6/2009 | Hibner et al. |
| 2010/0016713 A1 | 1/2010 | Welch |
| 2010/0019918 A1 | 1/2010 | Avital et al. |
| 2010/0183213 A1 | 7/2010 | Keppel et al. |
| 2010/0261997 A1 | 10/2010 | Ren et al. |
| 2010/0329419 A1* | 12/2010 | Blevis .............. 378/37 |
| 2011/0216880 A1 | 9/2011 | Blevis |
| 2011/0268339 A1 | 11/2011 | Volokh et al. |

OTHER PUBLICATIONS http://www.surgiceye.com/en/download/senses_flyer_eu_se6001-eu03_email.pdf, (5) pgs., Nov. 21, 2012.

Kambiz Rahbar, et al., Intraoperative 3-D Mapping of Parathyroid Adenoma Using Freehand SPECT, http://www.springerlink.com/content/0612m7575g01k73n/, (4) pgs., Sep. 27, 2012.

http://www.naviscan.com/images/stories/Naviscan_CE_Mark_Press_Release_Sept_8_BX_revised9.7.11.pdf, (1) pg., Sep. 8, 2011.

Product Overview, http://www.naviscan.com/products, (1) pg., Nov. 21, 2012.

Mayo Clinic—Molecular Breast Imaging: A Better Way to Spot Tumors in Dense Tissue, http://www.mayoclinic.org/news2009-mchi/5203.html, (1) pg., Mar. 10, 2009.

Gamma Medica (Index.html): http://www.gammamedica.com/, (2) pgs., Nov. 21, 2012.

Products & Services / Dilon Diagnostics, http://dilon.com/pages/products_and_services/4.php, (1) pg., Nov. 21, 2012.

Gamma Medico-Ideas Introduces New Tri-Modality FLEX Triumph™ Pre-Clinical Imaging System, http://www.gammamedica.com/pr_060830.html, (2) pgs., Aug. 30, 2006.

* cited by examiner

Patient Positioning

Breast Immobilization Plate

Initial Acquisition

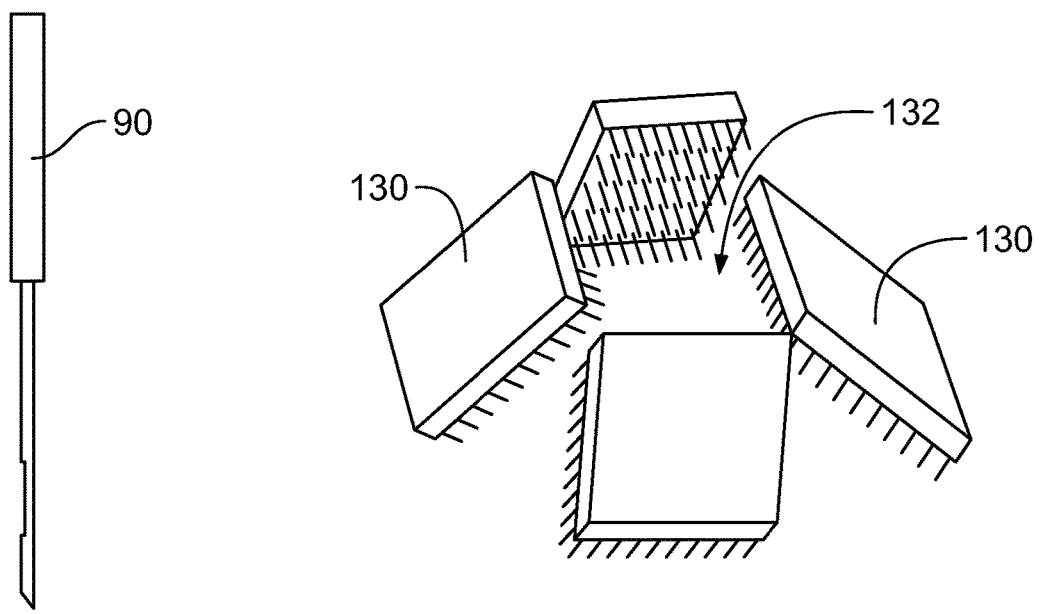
FIG. 8A
FIG. 8B
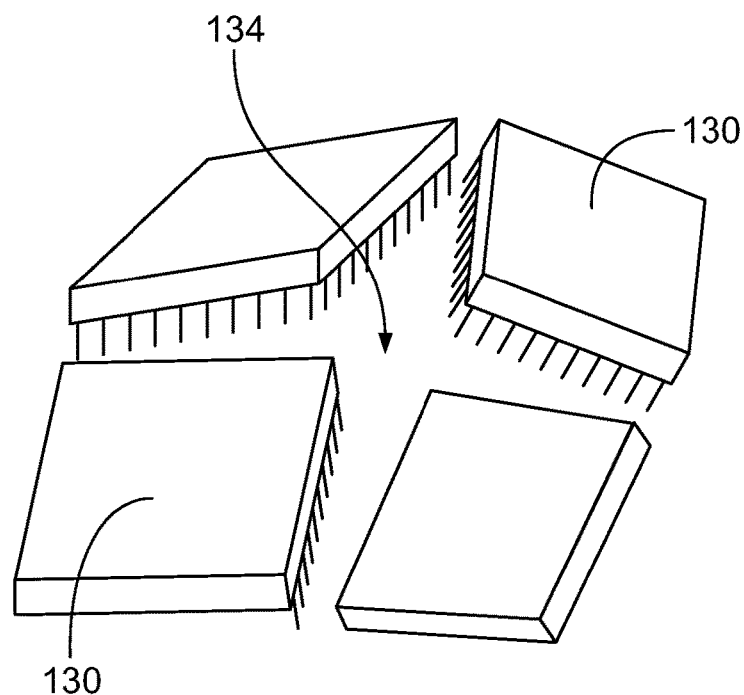
FIG. 9

SYSTEMS AND METHODS FOR BIOPSY GUIDANCE USING A BIOPSY UNIT INCLUDING AT LEAST ONE OF AN IMAGING DETECTOR OR ULTRASOUND PROBE CONCURRENTLY MOUNTED WITH A BIOPSY GUIDE

CROSS REFERENCE TO RELATED APPLICATIONS

This application claims priority to and the benefit of the filing date of U.S. Provisional Application No. 61/562,839 filed Nov. 22, 2011, the subject matter of which is hereby incorporated by reference in its entirety.

BACKGROUND OF THE INVENTION

The subject matter disclosed herein relates generally to nuclear medicine (NM) imaging systems, and more particularly to methods and systems for biopsy guidance in breast imaging with NM imaging systems, in particular Molecular Breast Imaging (MBI).

Mammography imaging is commonly used for the detection of breast cancer. Specifically, mammography imaging is used to detect lesions within the breast. Typically, the lesion is detected using three-dimensional imaging techniques. As such, a location and depth of the lesion can be determined from the image. The depth of the lesion aids, for example, in guiding a biopsy needle during extraction of a lesion sample for pathology.

However, some women cannot be effectively tested because of dense breasts and/or implants. Accordingly, these women may be tested using nuclear single photon imaging. Such imaging only provides two-dimensional images of the lesion having no depth information. When the depth of the lesion is unknown, guiding a biopsy needle is difficult and the chance of missing the lesion with the needle is increased, which is often high. As a result, a large number of samples may have to be taken, thereby causing pain and discomfort to the patient.

BRIEF DESCRIPTION OF THE INVENTION

In one embodiment, a breast imaging system is provided that includes a gantry and a breast immobilization plate mounted to the gantry, wherein the breast immobilization plate is configured to be coupled with a biopsy unit. The biopsy unit includes at least one nuclear medicine imaging detector in an angled orientation with respect to the breast immobilization plate. The breast imaging system also includes a nuclear medicine imaging detector mounted to the gantry parallel to the breast immobilization plate, wherein the nuclear medicine imaging detector mounted to the gantry and the breast immobilizing plate are configured to immobilize a breast therebetween.

In another embodiment, a breast imaging system is provided that includes a gantry and a breast immobilization plate mounted to the gantry, wherein the breast immobilization plate is configured to be coupled with a biopsy unit. The biopsy unit includes an ultrasound probe. The breast imaging system also includes a nuclear medicine imaging detector mounted to the gantry parallel to the breast immobilization plate, wherein the nuclear medicine imaging detector mounted to the gantry and the breast immobilizing plate are configured to immobilize a breast therebetween.

In yet another embodiment, a method for breast imaging is provided. The method includes immobilizing a breast between a breast immobilization plate and a first nuclear medicine imaging detector, positioning a second nuclear medicine imaging detector adjacent to the breast immobilization plate and parallel to the first nuclear medicine imaging detector for an initial acquisition period, and obtaining coarse lesion location information during the initial acquisition period. The method also includes moving the second nuclear medicine imaging detector from the breast immobilization plate and positioning a biopsy unit adjacent to the breast immobilization plate. The biopsy unit includes at least one nuclear medicine imaging detector in an angled orientation with respect to the breast immobilization plate and configured to acquire increased accuracy lesion location information. The method further includes using the increased accuracy lesion location information to guide a biopsy needle to the lesion.

BRIEF DESCRIPTION OF THE DRAWINGS

FIG. 8 is a diagram illustrating a detector arrangement in accordance with another embodiment.

FIG. 9 is a diagram illustrating a detector arrangement in accordance with another embodiment.

DETAILED DESCRIPTION OF THE INVENTION

Figure 1:
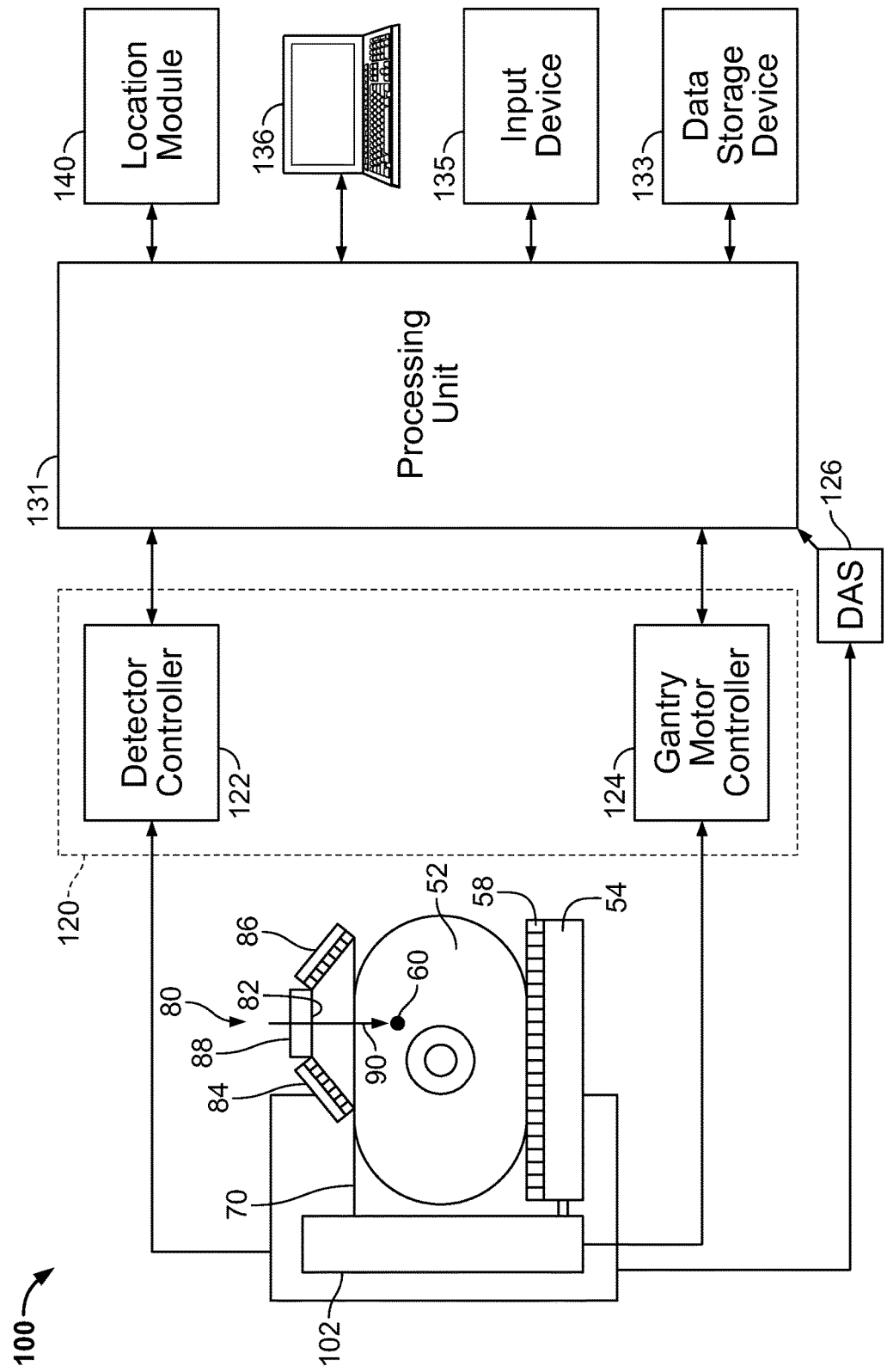
FIG. 1 is a schematic block diagram of an exemplary nuclear medicine (NM) imaging system constructed in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments described herein provide systems and methods for biopsy guidance in Nuclear Medicine (NM) imaging, particularly biopsy guidance for Molecular Breast Imaging (MBI). Various embodiments generally include a movable or removable detector head to allow use of a biopsy unit for guiding, for example, a biopsy needle into a lesion within a breast. By practicing various embodiments, biopsy guidance information is provided for guidance during a biopsy procedure, particularly for MBI.

FIG. 1 is a schematic block diagram of an NM imaging system 100 including a first detector 54 and a second detector 56 (shown in FIGS. 2 and 3) mounted on a gantry 102. The first and second detectors 54 and 56 are configured in some embodiments as a pair of nuclear medicine imaging detectors 54 and 56 (illustrated in an H-configuration) with at least one of the imaging detectors 54 and/or 56 movably or removably coupled to the gantry 102, which in the illustrated embodiment is the second imaging detector 56. In this embodiment, the second imaging detector 56 may be moved or removed and a biopsy unit 80 removably coupled to the gantry 102.

A breast immobilizing member is also provided, which in the illustrated embodiment is a breast immobilization plate 70 coupled to the gantry 102. The breast immobilizing plate 70 is coupled to the gantry 102 such that a breast 52 is immobilized between the immobilization plate 70 and the first detector 54 by moving at least one of the immobilization plate 70 and/or the first detector 54. The second detector 56 and the biopsy unit 80 are positionable adjacent to the immobilization plate 70, and may be coupled thereto using any suitable fastening means, such as a mechanical fastener (e.g., a bracket).

The first and second detectors 54 and 56 are arranged and operate to provide two-dimensional imaging of the breast 52, which in various embodiments is performed as part of an initial acquisition to estimate the location of a lesion 60 within the breast 52. In one or more embodiments, the estimate of the location is a coarse, rough or approximate location determination as described below (e.g., an estimate of the location). Each detector 54 and 56 generally captures a two-dimensional image that may be defined by the x and y location of a pixel and a detector number.

The first and second detectors 54 and 56 are illustrated as planar single photon imaging detectors, however, other configurations may be provided. In various embodiments, the first and second detectors 54 and 56 may be formed of cadmium zinc telluride (CZT) tiles or may any type of two-dimensional pixelated detector. The detectors 54 and 56 also include collimators 58 coupled thereto on a detection surface of the detectors 54 and 56, which are illustrated as parallel hole collimators 58. However, other types of collimators may be provided, such as diverging, converging, pinhole, cone-beam, fan-beam or slanted collimators, among others.

The biopsy unit 80 generally includes a support 82, which is illustrated as a support structure (e.g., a metal frame) configured to support thereon a pair of detectors 84 and 86 in an angled orientation with respect to the immobilization plate 70. The support 82 and immobilization plate 70 generally define a trapezoidal configuration having a biopsy guide 88 generally parallel to the immobilization plate 70. The biopsy guide 88 is configured to receive therethrough (e.g., in one or more openings) a biopsy instrument, such as a biopsy needle 90 for guiding into the breast 52 towards the lesion 60. The biopsy unit 80 may be offset slightly from the immobilization plate 70 to allow the biopsy needle 90 to pass by the immobilization plate 70. However, in some embodiments, the immobilization plate 70 may be configured having one or more openings for receiving therethrough the biopsy needle 90.

Each of the detectors 54 and 56 has a radiation detection face that is directed towards the breast 52 immobilized therebetween. This configuration provides general location information for a lesion 60 within the breast 52. The detectors 84 and 86 then may be used for more precise or accurate lesion 60 location (e.g., increased accuracy lesion location information). In particular, the detectors 84 and 86 are positioned generally in the area of the lesion 60 based on the coarse location information (e.g., coarse lesion location information) such that the detectors 84 and 86 are focused on a structure of interest, which in this embodiment is the lesion 60 within the breast 52. The radiation detection faces of the detectors 84 and 86 are also covered by collimators 58 as described above. An actual field of view (FOV) of each of the detectors 54 and 56 may be directly proportional to the size and shape of the respective imaging detector, or may be changed using the collimator 58.

A motion controller unit 120 may control the movement and positioning of the gantry 102 and/or the detectors 54 and 56 or immobilization plate 70 with respect to each other to position the breast 52 within the FOVs of the imaging detectors 54 and 56 prior to acquiring an image of the breast 52. The controller unit 120 may have a detector controller 122 and gantry motor controller 124 that may be automatically commanded by a processing unit 131, manually controlled by an operator, or a combination thereof. The gantry motor controller 124 and the detector controller 122 may move the gantry 102 or detectors 54 and 56, as well as the immobilization plate 70 with respect to the breast 52, with the distance between the detectors 54 and 56 registered by the controller 120 and used by the processing unit 131 during data processing. In some embodiments, motion is manually achieved and the controller 120 is replaced with scales or preferably encoders for measuring at least the distance between the detectors 54 and 56, as well as the compression force exerted by at least one of the immobilization plate 70 and/or the detector 54 on the breast 52.

In operation, the detectors 54 and 56 and gantry 102 remain stationary after being initially positioned to provide an initial acquisition mode. The imaging data may then be used to position the biopsy unit 80, which acquires a more focused image, such as a reconstructed composite image comprising 2D images and depth information.

A Data Acquisition System (DAS) 126 receives analog and/or digital electrical signal data produced by the detectors 54, 56, 84 and/or 86 and decodes the data for subsequent processing in the processing unit 131. A data storage device 133 may be provided to store data from the DAS 126 or reconstructed image data. An input device 135 also may be provided to receive user inputs and a display 136 may be provided to display reconstructed images.

The NM imaging system 100 also includes a location module 140 configured to perform one or more location determination methods, for example, to determine the location (e.g., coarse depth location) of the lesion 60 in the breast 52. Although FIG. 1 shows the location module 140 as a module separate from the processing unit 131, it should be appreciated that the location module 140 can also be a program, software, or the like stored on a computer readable medium to be read by the NM imaging system 100.

Figure 2:
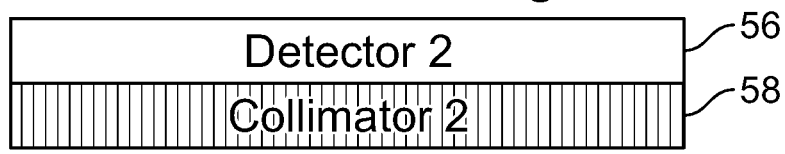
FIG. 2 is a diagram illustrating detectors in accordance with various embodiments in a patient positioning position.
Figure 2:
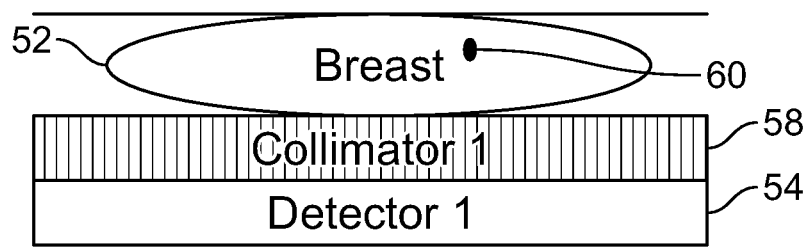
Figure 3:
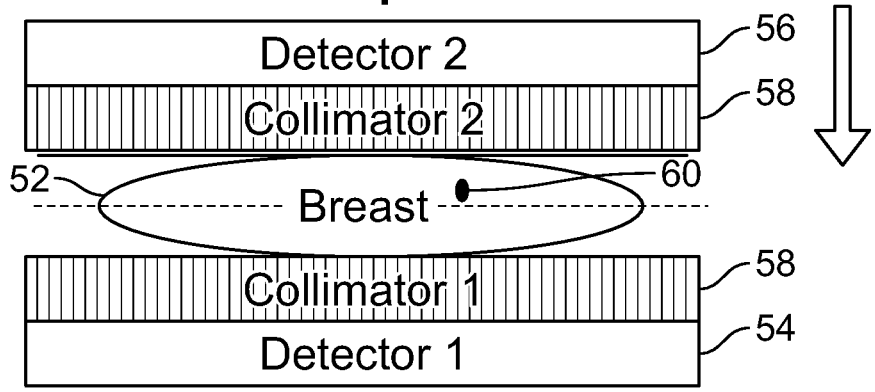
FIG. 3 is a diagram illustrating detectors in accordance with various embodiments in an initial acquisition position.

In operation, as shown in FIGS. 2 and 3, the breast 52 is initially positioned between the first detector 54 and the immobilization plate 70 with the immobilization plate 70 moved to immobilize the breast 52 therebetween. In various embodiments, the distance between the first detector 54 and the immobilization plate 70 may be changed to accommodate breasts with different sizes and to immobilize the breast 52 for the duration of lesion location determination and a subsequent biopsy procedure by applying light pressure. The distance between near faces of the collimators 58 is registered automatically or manually. Thus, the detector 54 and the immobilization plate 70 are used to apply an immobilizing force to the breast 52. Accordingly, in one embodiment, the breast 52 is positioned between the detector 54 and the immobilization plate 70 with the immobilization plate 70 translated to lightly compress and/or maintain the position of the breast 52 between the detector 54 and the immobilization plate 70 (e.g., slightly compressed at a pressure less than the pressure applied during an x-ray mammography exam). It should be noted that the immobilization and/or compression of the breast 52 shown in the various figures is exaggerated for illustration. Thus, the distance between the faces of the collimator 58 of the first detector 54 and the immobilization plate 70 in various embodiments is equal to the thickness of the slightly compressed breast, which is registered and may be used by a data analysis program.

Once the breast 52 is immobilized, the second detector 56 may be moved (e.g., translated) into position as illustrated by the arrow in FIG. 3 until the second detector 56 abuts or is proximate to the immobilization plate 70 (e.g., contacting or slightly spaced from the immobilization plate 70). Image information is then acquired to determine a coarse lesion 60 location, which in various embodiments includes the X and Y location of the lesion 60 and a rough or approximate (coarse) Z location estimation of the location of the lesion 60, such as whether the lesion 60 is on the upper or lower section of the breast 52 (illustrated by the dashed line). The location information may be determined, for example, based on the apparent location of the imaged lesion 60 by each of the detectors 54 and 56 and the using geometry to approximate the location.

Figure 4:
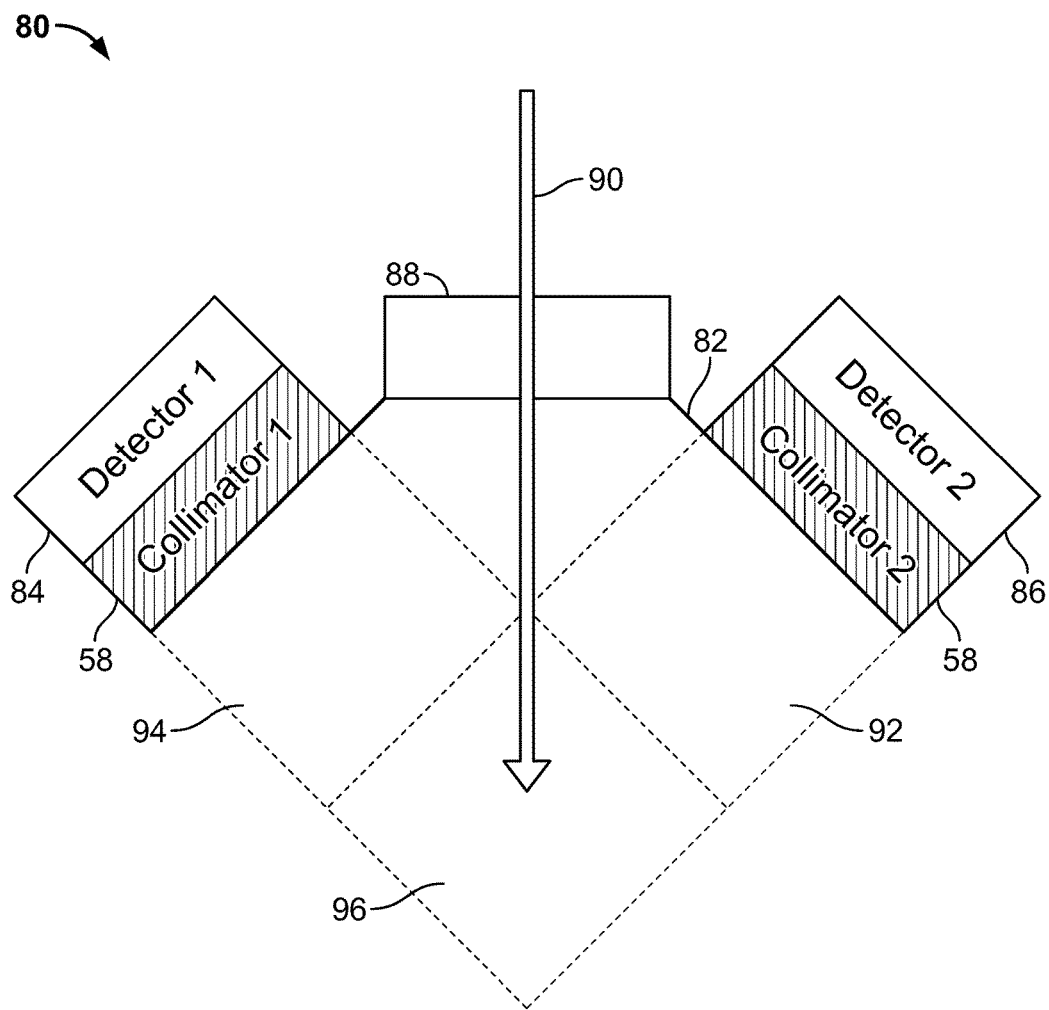
FIG. 4 is a block diagram of a biopsy unit in accordance with various embodiments.

The position data of the lesion 60 from the initial acquisition then may be used for positioning of the biopsy unit 80. In particular, the second detector 56 is moved away from the immobilization plate 70 and may be removed from the gantry 102 in some embodiments. However, in some embodiments the second detector 56 is only moved out of the area above the immobilization plate 70 to allow coupling thereto of the biopsy unit 80. The biopsy unit 80 is generally coupled to the gantry 102 or to the immobilization plate 70 such that fields of view 92 and 94 of the detectors 84 and 86 are directed toward the object of interest, namely the lesion 60 within a common field of view 96 to provide more detailed or exact lesion 60 location information, such as by triangulation as shown in FIG. 4.

Figure 5:
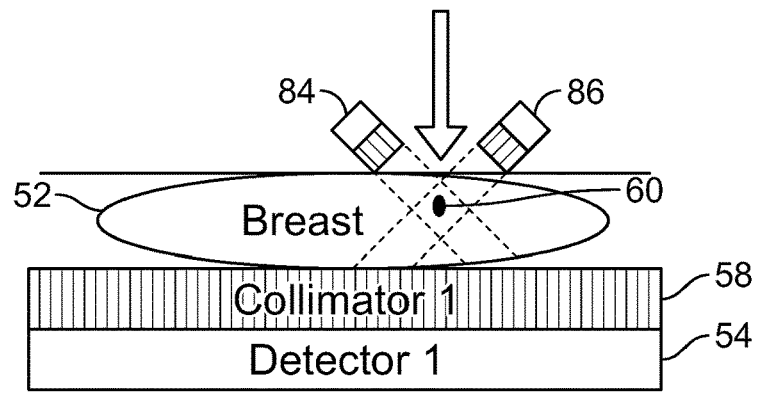
FIG. 5 is a diagram illustrating biopsy guidance in accordance with one embodiment.

Thus, an integrated self-contained biopsy unit 80 may be provided for biopsy guidance as shown in FIG. 5. As shown therein, in some embodiments, position data from an initial acquisition is used only for determining where to position the biopsy unit 80. Thereafter, needle 90 positioning is determined by triangulation from the biopsy unit 80, such as based on acquired emission data or gamma radiation activity count data from an agent, such as a radiopharmaceutical or radioactive tracer, injected within the patient (e.g., injected into the breast).

It should be noted that one of the detectors 84 and/or 86 may be rotated such that the detector is 90 degrees to the depth of the lesion 60, namely generally perpendicular to the immobilization plate 70.

Figure 6:
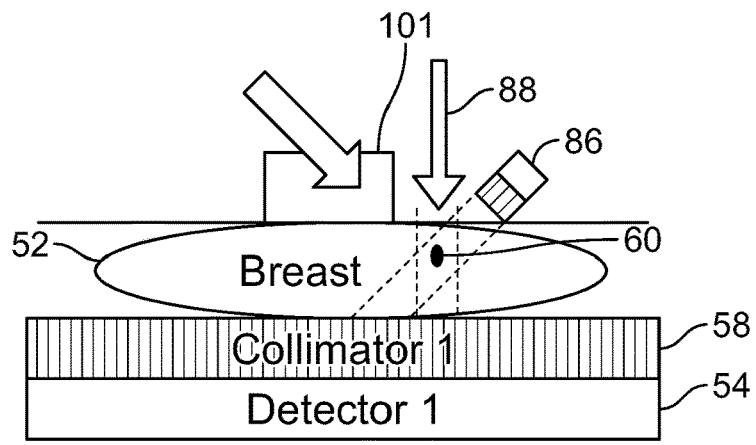
FIG. 6 is a diagram illustrating biopsy guidance in accordance with another embodiment.

Variations and modifications are contemplated. For example, as shown in FIG. 6, only one of the detectors 86 is provided and the detector 84 removed. In this embodiment, the needle 90 may be guided using the biopsy guide 88 or a biopsy guide 101 that is angled and generally replaces the detector 84. In this embodiment, needle positioning may be provided from triangulation based on combined detector 54 and biopsy unit data from the detector 86. In this embodiment, flexibility is provided in that the direction or orientation of the needle 90 may be varied.

Figure 7:
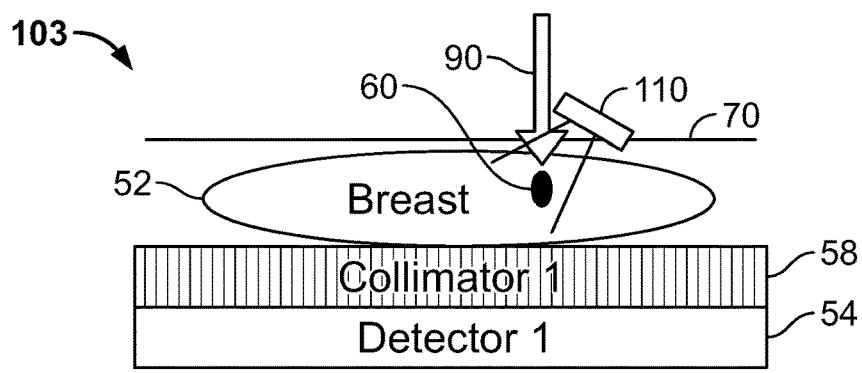
FIG. 7 is a diagram illustrating a biopsy unit in accordance with another embodiment.

In another embodiment, as shown in FIG. 7, an ultrasound hybrid biopsy arrangement 103 may be provided. In the illustrated embodiment, the biopsy unit 80 includes an ultrasound probe 110 instead of the detectors 84 and 86. In this embodiment, X and Y position data of the lesion 60 is determined from the detector 54 and used for positioning the ultrasound probe 110. It should be noted that any suitable support structure may be provided to support the ultrasound probe 110. In some embodiments, an actuator may be provided and used to mechanically move, which may be automatic, the ultrasound probe 110. In other embodiments, the ultrasound probe 110 in manually moved, for example, by an operator.

In this embodiment, needle positioning information is determined using combined data from the detector 54 and the ultrasound probe 110 (e.g., ultrasound image data). The ultrasound probe 110 provides real-time and/or an online view of the needle 90, which may provide the automatic guidance of the needle 90. It should be noted that the detector 56 is moved away from the immobilization plate 70, such as to a highest point, providing space for the ultrasound probe 110 and performing biopsy guidance. In various embodiments, the detector 56 in combination with the detector 54 is similarly used for an initial acquisition to determine an approximate or coarse location of the lesion 60. Thus, an approximate or coarse location of the lesion 60 may be determined using one or more of the detectors 54 and 56 and then guidance of the needle 90 provided using the ultrasound probe 110 using real-time image feedback.

Different configurations and numbers of detector modules may be provided. For example, more than two detector modules and more than one plane of response may be used to increase the sensitivity and speed of visualization. In particular, as shown in FIG. 8, a plurality of detector modules 130 is arranged in a square configuration having an opening 132 therethrough. It should be noted that the detector modules 130 are angled, such as focused towards an object of interest. For example, each of the detector modules 130 is arranged with one edge perpendicular to an adjacent detector module 130. Each of the detector modules 130 are then arranged in a tilted orientation, which in this embodiment is angled outward and downward from the opening 132 (as viewed in FIG. 8). The opening 132 allows for passage therethrough of the needle 90. In some embodiments, a needle support structure (as described in more detail herein)

may be provided within the opening 132 to aid in guiding or maintaining a trajectory of the needle 90.

As another example, shown in FIG. 9, the detector modules 130 may be positioned such that corners are pointed inward toward a point to define an opening 134. The detector modules 130 are similarly angled as in FIG. 8. For example, a lower corner of each detector module 130 is proximate to or abuts the corner of an adjacent detector module 130 with each module 130 also tilted in addition to being angled. For example, each of the detector modules 130 may be angled outward and downward from the opening 134 (as viewed in FIG. 9), but instead of each of the two corners along one edge (the top edge as viewed in FIG. 8) of each detector module 130 being positioned proximate to or abutting corners of adjacent detector modules 130, diagonally opposite corners of each detector module 130 are positioned proximate to or abutting corners of adjacent detector modules 130. Thus, the detector modules 130 in the configuration of FIG. 8 are arranged to be aligned in as squares (in an up/down direction as viewed in FIG. 8) and the detector modules 130 in the configuration of FIG. 9 are arranged to be aligned as diamonds (in an up/down direction as viewed in FIG. 9). The opening 134 also similarly allows passage therethrough of the needle 90. In some embodiments, a needle support structure (as described in more detail herein) may be provided within the opening 134 to aid in guiding or maintaining a trajectory of the needle 90.

Figure 10:
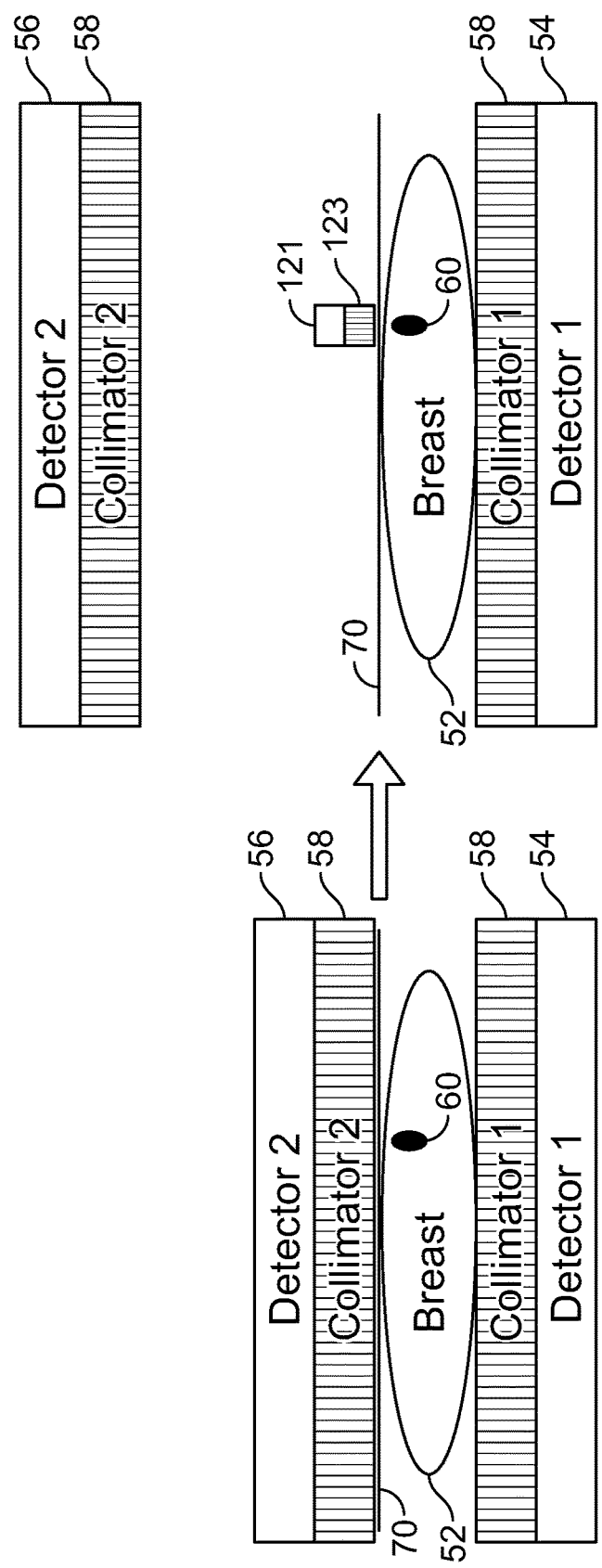
FIG. 10 is a diagram illustrating a detector arrangement in accordance with another embodiment.

Some embodiments provide configurations for imaging and not necessarily for biopsy guidance such as shown in FIG. 10. In this embodiment, the two detector arrangement using detectors 54 and 56 may provide inconclusive findings with respect to a suspected lesion 60. Thereafter, the detector 56 is moved away from or decoupled and a smaller detector module 121 is used, which is generally narrower than the detector 54 or 56 and may be similar to the detectors 84 and 86. However, in this embodiment, the detecting face of the detector module 121 is positioned generally parallel to the detection area, namely parallel to the immobilization plate 70. In this embodiment, the detector module 121 includes a high resolution collimator 123, such as having longer bores than the collimator 58, converging bores, etc. In this embodiment, a local optimization of resolution may be provided. However, it should be appreciated that in various embodiments, the detector module 121 with the collimator 123 may be any combination that generally provides higher resolution that the detectors 54 and 56.

Other variations and modifications are contemplated. For example, the angles of the detectors or the collimators may be adjusted to focus the detector closer or farther from the apparatus. Additionally, different types of collimators may be provided, such as parallel hole (straight and/or slanted), converging, diverging, pinhole, or coded aperture collimators, among others. Also, tomography of the focal plane (or focal point) may be used to reduce background.

Accordingly, various embodiments provide one or more methods for biopsy guidance or breast imaging, which includes determining or approximating the location of a lesion within the breast and then providing guidance of, for example, a needle into the breast.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software, which may be a tangible non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A breast imaging system comprising:
a gantry;
a breast immobilization plate mounted to the gantry;
a biopsy unit configured to be coupled with the breast immobilization plate, the biopsy unit including a support frame, a biopsy guide configured to accept a biopsy needle, and a pair of nuclear medicine imaging detectors, the pair of nuclear medicine imaging detectors in an angled orientation with respect to the breast immobilization plate, the pair of nuclear medicine imaging detectors being two-dimensional pixelated detectors, the biopsy guide disposed between the pair of nuclear medicine imaging detectors, the pair of nuclear medicine imaging detectors defining an opening through which the biopsy needle is configured to pass, wherein the biopsy guide is mounted to the support frame generally parallel to the breast immobilization plate; and
a first nuclear medicine imaging detector mounted to the gantry parallel to the breast immobilization plate, the nuclear medicine imaging detector mounted to the gantry and the breast immobilizing plate configured to immobilize a breast between the breast immobilizing plate and the first nuclear medicine imaging detector, the first nuclear medicine imaging detector being a two-dimensional pixelated detector;
wherein the breast immobilization plate is configured to be coupled to a second nuclear medicine imaging detector in a parallel orientation with respect to the breast immobilization plate, wherein the second nuclear medicine imaging detector is opposed to the first nuclear medicine imaging detector and parallel to the first nuclear medicine imaging detector, the second nuclear medicine imaging detector being a two-dimensional pixelated detector, and wherein the pair of nuclear medicine imaging detectors of the biopsy unit comprises a detector having a higher resolution than the first nuclear medicine imaging detector.

2. A breast imaging system comprising:
a gantry;
a breast immobilization plate mounted to the gantry;
a biopsy unit configured to be coupled with the breast immobilization plate, the biopsy unit including a support frame, a biopsy guide configured to accept a biopsy needle, and a pair of nuclear medicine imaging detectors, the pair of nuclear medicine imaging detectors in an angled orientation with respect to the breast immobilization plate, the pair of nuclear medicine imaging detectors being two-dimensional pixelated detectors, the biopsy guide disposed between the pair of nuclear medicine imaging detectors, the pair of nuclear medicine imaging detectors defining an opening through which the biopsy needle is configured to pass, wherein the biopsy guide is mounted to the support frame generally parallel to the breast immobilization plate; and
a first nuclear medicine imaging detector mounted to gantry parallel to the breast immobilization plate, the nuclear medicine imaging detector mounted to the gantry and the breast immobilizing plate configured to immobilize a breast between the breast immobilizing plate and the first nuclear medicine imaging detector, the first nuclear medicine imaging detector being a two-dimensional pixelated detector;
wherein the breast immobilization plate is configured to be coupled to a second nuclear medicine imaging detector in a parallel orientation with respect to the breast immobilization plate, wherein the second nuclear medicine imaging detector is opposed to the first nuclear medicine imaging detector and parallel to the first nuclear medicine imaging detector, the second nuclear medicine imaging detector being a two-dimensional pixelated detector, and wherein the second medicine imaging detector coupled to the breast immobilization plate is configured to acquire coarse lesion location information for a lesion within the breast and wherein the pair of nuclear medicine imaging detectors are configured to acquire increased accuracy lesion location information for the lesion, wherein the increased accuracy lesion location information has a higher resolution than the coarse lesion location information.

3. A method for breast imaging, the method comprising:
immobilizing a breast between a breast immobilization plate and a first nuclear medicine imaging detector, the first nuclear medicine imaging detector being a two-dimensional pixelated detector;
positioning a second nuclear medicine imaging detector adjacent to the breast immobilization plate and parallel to the first nuclear medicine imaging detector for an initial acquisition period, the second nuclear medicine imaging detector being a two-dimensional pixelated detector;
obtaining, with the first and second nuclear medicine imaging detectors, coarse lesion location information during the initial acquisition period;
moving the second nuclear medicine imaging detector from the breast immobilization plate after obtaining the coarse lesion location information;
positioning a biopsy unit adjacent to the breast immobilization plate using the coarse lesion location information, the biopsy unit including a support frame, a biopsy guide, and a pair of nuclear medicine imaging detectors, the pair of nuclear medicine imaging detectors in an angled orientation with respect to the breast immobilization plate, the pair of nuclear medicine imaging detectors being two-dimensional pixelated detectors, the biopsy guide disposed between the pair of nuclear medicine imaging detectors, the pair of nuclear medicine imaging detectors defining an opening through which the biopsy needle is configured to pass, wherein the biopsy guide is mounted to the support frame generally parallel to the breast immobilization plate, the pair of nuclear medicine imaging detectors configured to acquire increased accuracy lesion location information, wherein the increased accuracy lesion location information has a higher resolution than the coarse lesion location information; and using the increased accuracy lesion location information to guide the biopsy needle to a lesion via the biopsy guide.

4. The method of claim 3, wherein the biopsy guide and at least a portion of the pair of nuclear medicine imaging detectors are disposed a distance from a surface of the object being imaged and the breast immobilization plate.

5. The method of claim 3, further comprising replacing the pair of nuclear medicine imaging detectors with an ultrasound probe.

6. The method of claim 3, wherein obtaining coarse lesion location information comprises obtaining an x and y location of the lesion and a coarse z or depth location of the lesion.

* * * * *